United States Patent
Tsai

(10) Patent No.: US 8,524,486 B2
(45) Date of Patent: Sep. 3, 2013

(54) **CULTURE METHOD OF *AANTRODIA CAMPHORATA***

(76) Inventor: Ta-Ming Tsai, Taoyuan County (TW)

( * ) Notice: Subject to any disclaimer, the term of this patent is extended or adjusted under 35 U.S.C. 154(b) by 1361 days.

(21) Appl. No.: 11/907,985

(22) Filed: Oct. 19, 2007

(65) Prior Publication Data

US 2008/0102512 A1    May 1, 2008

(30) Foreign Application Priority Data

Oct. 27, 2006  (TW) ............................... 95139686 A

(51) Int. Cl.
*A01G 1/04* (2006.01)
(52) U.S. Cl.
USPC ........................ 435/256.8; 47/1.1; 435/254.1
(58) Field of Classification Search
None
See application file for complete search history.

(56) References Cited

U.S. PATENT DOCUMENTS 6,740,517 B2 *   5/2004   Lan et al. .................. 435/254.3

OTHER PUBLICATIONS

Royse et al., Interdisciplinary Science Reviews. vol. 10, No. 4, 1985 329.*
Hatvani et al., Process Biochemistry 37 (2001) 491-496.*

* cited by examiner

*Primary Examiner* — Irene Marx
(74) *Attorney, Agent, or Firm* — Bacon & Thomas, PLLC

(57) ABSTRACT

A culture method of a fruiting body of *Antrodia camphorata* is provided, which includes: (a) fermenting a culture medium containing yeast at 5-35° C. for 3-30 days; (b) adding wood flour to the fermented culture medium with stirring; (c) placing the wood flour and the culture medium into a vessel; (d) sterilizing the vessel containing the wood flour and the culture medium; (e) inoculating *Antrodia camphorata* strains into the sterilized vessel containing the wood flour and the culture medium, and culturing at 5-35° C., to form mycelia; (f) inoculating the wood flour containing *Antrodia camphorata* mycelia into a wood segment; (g) placing the wood segment inoculated with *Antrodia camphorata* mycelia in an environment where the temperature is 5-35° C. and the humidity is 65-85%, and culturing for a period of time; and (h) removing the wood flour remained on the wood segment, then placing the wood segment in an environment where the temperature is 15-35° C. and the humidity is 80-98%, and culturing for a period of time, to form a fruiting body of *Antrodia camphorata*. A culture method of *Antrodia camphorata* mycelia, a culture method of a fruiting body of *Antrodia camphorata*, and a fruiting body of *Antrodia camphorata* cultured by the same method are also provided. The fruiting body of *Antrodia camphorata* cultured by the method of the present invention is thick and solid, and the content of triterpenoids is comparable to that of wild *Antrodia camphorata*.

5 Claims, 7 Drawing Sheets

CULTURE METHOD OF AANTRODIA CAMPHORATA

TECHNICAL FIELD

The present invention relates to a culture method of *Antrodia camphorata*, which includes inoculating *Antrodia camphorata* strains into a wood segment to culture a fruiting body of *Antrodia camphorata* in large scale.

BACKGROUND OF THE INVENTION

*Antrodia camphorata* is also called Niu Zang Zhi or Niu Zang mushroom (*Antrodia cinnamomea*), which belongs to genus *Antrodia*, family Polyporaceae, order Aphyllophorales, and is a perennial mushroom and a specific fungus in Taiwan. It only parasitizes in the inner wall of the hollow trunk of *Cinnamomum kanehirae* Hayata or on the moist surface of the dead, rotting trunk of *Cinnamomum kanehirae* Hayata in a mountainous area of Taiwan in the altitude of 200 meters to 2000 meters. As the main aromatics in *Cinnamomum kanehirae* Hayata are terpenoids, not camphor, which are aromatic compounds present in *Cinnamomum camphora* (L.) Presl, the once used scientific name *Antrodia camphorata* for *Cinnamomum kanehirae* Hayata was corrected as *Antrodia cinnamomea* by Mushroom cultivation experts Dongzhu Zhang and Wenneng Zhou.

The fruiting body of *Antrodia camphorata* is grown from the hollow trunk of *Cinnamomum kanehirae* Hayata with an initial flat shape, and grows by adhering to the inner surface of the trunk, and then the anterior edge of the fruiting body curls away from the trunk and is warped upwards, and forms a horseshoe shape or irregular shape. The longer the fruiting body grows, the closer the contact is, and it is lignified or suberized gradually. The fruiting body is in a platy-shaped or bell-shaped appearance and has a strong bitter smell. The upper surface of the annual or perennial fruiting body is tangerine, orange-brown to light flesh colored, then turns into brown. The surface is smooth and has concentric circles, and the ostioles are in the shape of circle or polygon and have spores therein. The fresh surface of the ostioles of the fruiting body is tangerine, orange-brown to light flesh colored, and the aged surface is reddish-brown colored.

Due to the detoxification for food poisoning, diarrhea, vomit, pesticide poisoning and so on, *Antrodia camphorata* is an excellent antidote and also considered to have desired effect on cancer or chronic diseases. Common fungus cannot grow on a camphor tree, as it has strong fragrance and can repel insects, only *Antrodia camphorata* can parasitize on *Cinnamomum kanehirae* Hayata indigenous to Taiwan, not similar tress, such as, common camphor tree, and *Cinnamomum Camphora*. Therefore, the productivity of *Antrodia camphorata* is scarce. Further, *Cinnamomum kanehirae* Hayata, on which *Antrodia camphorata* grows, is a first class protected tree species, and it is forbidden to harvest *Antrodia camphorata* as an appendix, thus *Antrodia camphorata* is in shortage and cannot meet the demand of the market. Therefore *Antrodia camphorata* is also called "Taiwan Ruby", only produced in Nanzhuang, Miaoli, and Liugui, Gaoxiong, and so on.

The therapeutic effects of *Antrodia camphorata* for chronic diseases and cancer have been recognized and accepted from long time ago, thus further increasing the price of *Antrodia camphorata* in the market. In fact, it has been indicated by scientific research works that the ability of *Antrodia camphorata* to kill the lymphoma cells p-388 of mouse is remarkable. The hot-water soluble polysaccharides in *Antrodia camphorata* mycelia can stimulate lymphocyte in the blood of a normal adult to produce cytokine to kill human lymphoma U-937 cells, and also can increase the phagocytosis ability of macrophage, promote the proliferation of splenocytes and the secretion of interleukin IL-5. Additionally, *Antrodia camphorata* also can inhibit the growth of *Streptococcus aureus* and *Trichophytone mentagrophytes* as well as numerous intestinal floras. Generally, *Antrodia camphorata* has the effects of purifying the blood, removing toxic substances, tonifying kidney, protecting liver, regulating intestine, strengthening the heart, adjusting blood pressure, building body, resisting cold, anti bacteria, suppressing cough, eliminating sputum, alleviating pain, tranquilizing, anti cancer, relieving tumor, expelling toxin, and so on, thus it is a medicinal fungus with extensive effectiveness.

For the purpose of popularizing the use of *Antrodia camphorata*, stabilizing the high price in the market, and maintaining the long-term protection of *Cinnamomum kanehirae* Hayata, large-scaled artificial culture of *Antrodia camphorata* is a major bottleneck to be broken through by many related industries. Currently, most of the artificial culture methods of *Antrodia camphorata* include culturing mycelia by liquid fermentation or solid fermentation, then inoculating the strains in a space bag, to grow a fruiting body of *Antrodia camphorata*. However, the growth of the mycelia is not well when being cultured by the existing technology, and the inclusion is loose and miscellaneous fungus is likely to grow when the fruiting body is cultured indoors by using the space bag. Additionally, compared with the fruiting body of wild Antrodia camphorata, the fruiting body of *Antrodia camphorata* cultured by using the space bag is thinner, and the content of triterpenoids is significant hard from that of wild *Antrodia camphorata*. Further, the space bag is difficult to be degraded in the soil, thus causing an environmental issue. Nowadays, although space bags made of biodegradable material are available, they are undoubtedly a burden on the cost of applying in the large-scaled culture of fungus and mushrooms due to the high price. Most importantly, when infecting a wood segment the spore of wild *Antrodia camphorata* can only infect *Cinnamomum kanehirae* Hayata and parasitize therein to form a fruiting body due to the obvious host specificity. For the existing technology, artificial cultured *Antrodia camphorata* mycelia cannot infect the wood segments of different tree species. Therefore, the culture of the fruiting body is carried out directly by using the wood segment of wild *Cinnamomum kanehirae* Hayata infected with the spore of *Antrodia camphorata*. However, this artificial culture method is not suitable for growing *Antrodia camphorata* culture with a lot of solid fruiting body, and the contents of triterpenoids and polysaccharides are also limited.

As most of the commercial available fruiting bodies are thin annual fungi, and thick and solid perennial ones are rare, there is a large demand for *Antrodia camphorata* in the market. However, it is difficult to get natural wild *Antrodia camphorata*, thus there is an extremely large pressure in harvest. Therefore, developing an artificial culture method of *Antrodia camphorata* with a thick and solid fruiting body and enriched with triterpenoids by a wood segment, so as to effectively supply *Antrodia camphorata* with good quality, is a technical field deserving further study in the field.

SUMMARY OF INVENTION

*Antrodia camphorata* is a specific fungus in Taiwan, also called Niu Zang mushroom (*Antrodia cinnamomea*), and only grows in *Cinnamomum kanehirae* Hayata, which is a protected plant in Taiwan. Therefore, it is very difficult to harvest Antrodia camphorata grown in hollow trunk of *Cinnamomum kanehirae* Hayata, and the production is very small as well. Accordingly, the present invention is directed to provide a solid culture method of *Antrodia camphorata* mycelia, which includes inoculating *Antrodia camphorata* strains into a vessel containing a yeast culture medium and wood flour, and culturing to obtain *Antrodia camphorata* mycelia.

The present invention is further directed to provide a liquid culture method of *Antrodia camphorata* mycelia, which includes inoculating *Antrodia camphorata* strains into a vessel containing a yeast culture medium, and culturing to obtain *Antrodia camphorata* mycelia.

The present invention is further directed to provide a culture method of a fruiting body of *Antrodia camphorata*, which includes inoculating a matrix containing *Antrodia camphorata* mycelia into a wood segment, and culturing for a period of time, to obtain the fruiting body of *Antrodia camphorata*.

The present invention is further directed to provide a fruiting body of *Antrodia camphorata* cultured according to the culture method of the fruiting body of *Antrodia camphorata*, which is abundant in triterpenoids and is a medicinal fungus that has a promising potential bioavailability.

For the above purposes, the present invention provides a solid culture method of *Antrodia camphorata* mycelia, which includes: (a) fermenting a culture medium containing yeast at 5-35° C. for 3-30 days; (b) adding wood flour to the fermented culture medium with stirring; (c) placing the wood flour and the culture medium into a vessel; (d) sterilizing the vessel containing the wood flour and the culture medium; and (e) inoculating *Antrodia camphorata* strains into the sterilized vessel containing the wood flour and the culture medium, and culturing at 5-35° C., to obtain *Antrodia camphorata* mycelia.

Preferably, the culture medium in Step (a) contains 1-8% of sugar, 0.06-1.2% of yeast, 0.01-0.4% of magnesium sulfate, and 0.01-0.4% of potassium dihydrogen phosphate. The culture medium containing yeast is required to be fermented for 7-14 days.

Preferably, the culture in Step (c) is carried out in a vessel of a humidity of 60-90% (most preferably, 80%).

Preferably, *Antrodia camphorata* strains in Step (e) are cultured at 20-30° C.

The present invention further provides a liquid culture method of *Antrodia camphorata* mycelia, which includes: (a) fermenting a culture medium containing yeast at 5-35° C. for 3-30 days; (b) placing the fermented culture medium into a vessel; (c) sterilizing the vessel containing the culture medium; and (d) inoculating *Antrodia camphorata* strains into the sterilized culture medium, and culturing at 5-35° C., to obtain *Antrodia camphorata* mycelia.

Preferably, the culture medium in Step (a) contains sugar, yeast, magnesium sulfate, and potassium dihydrogen phosphate, and more preferably contains 1-8% of sugar, 0.06-1.2% of yeast, 0.01-0.4% of magnesium sulfate, and 0.01-0.4% of potassium dihydrogen phosphate. The culture medium containing yeast is required to be fermented for 7-14 days.

Preferably, *Antrodia camphorata* strains in Step (d) are cultured at 20-30° C.

The present invention further provides a culture method of a fruiting body of *Antrodia camphorata*, which includes: (a) inoculating a matrix containing *Antrodia camphorata* mycelia into a wood segment; (b) placing the wood segment inoculated with *Antrodia camphorata* mycelia in an environment where the temperature is 5-35° C. and the humidity is 65-85%, and culturing for a period of time; and (c) removing the matrix remained on the wood segment, then placing the wood segment in an environment where the temperature is 15-35° C. and the humidity is 80-98%, and culturing for a period of time, to obtain a fruiting body of *Antrodia camphorata*.

Preferably, the matrix containing *Antrodia camphorata* mycelia in Step (a) includes a solid matrix or a liquid matrix, and the solid matrix can be wood flour.

Preferably, the wood segment in Step (b) is cultured in an environment where the temperature is 25-30° C. and the humidity is 75-85% for at least more than one month.

Preferably, the culture in Step (c) is carried out in an environment where the temperature is 26-30° C. and the humidity is 80-98%, and the culture time is at least more than three months.

Preferably, the cultures in Step (b) and (c) are carried out in an environment where the concentration of $CO_2$ is lower than 2%.

The present invention further provides a culture method of *Antrodia camphorata*, which includes: (a) fermenting a culture medium containing yeast at 5-35° C. for 3-30 days; (b) adding wood flour to the fermented culture medium with stirring; (c) placing the wood flour and the culture medium into a vessel; (d) sterilizing the vessel containing the wood flour and the culture medium; and (e) inoculating *Antrodia camphorata* strains into the sterilized vessel containing the wood flour and the culture medium, and culturing at 5-35° C., to obtain *Antrodia camphorata* mycelia; (f) inoculating the wood flour containing *Antrodia camphorata* mycelia into a wood segment; (g) placing the wood segment inoculated with *Antrodia camphorata* mycelia in an environment where the temperature is 5-35° C. and the humidity is 65-85%, and culturing for a period of time; and (h) removing the wood flour remained on the wood segment, then placing the wood segment in an environment where the temperature is 15-35° C. and the humidity is 80-98%, and culturing for a period of time, to form a fruiting body of *Antrodia camphorata*.

Preferably, the humidity in the vessel in Step (c) is 60-90%, and more preferably 80%.

Preferably, the wood segment in Step (g) is cultured in an environment where the temperature is 25-30° C., the humidity is 75-85%, and the concentration of $CO_2$ is lower than 2%.

Preferably, the wood segment in Step (h) is cultured in an environment where the temperature is 26-30° C., the humidity is 90-98%, and the concentration of $CO_2$ is lower than 2%.

Preferably, the culture time of the wood segment in Step (g) is at least more than one month.

Preferably, the culture time of the fruiting body of *Antrodia camphorata* in Step (h) is at least more than three months.

The present invention further provides a fruiting body of *Antrodia camphorata* cultured according to the culture method of *Antrodia camphorata*.

From the above description, the culture method of *Antrodia camphorata* of the present invention inoculates *Antrodia camphorata* mycelia cultured by using an artificial fermented culture medium into wood segments from numerous tree specie, thus breaking the parasitized host specificity and achieving the object of massive culture of the fruiting body of *Antrodia camphorata*, thereby meeting the urgent demand for *Antrodia camphorata* in the market, and broadening the scope of application in biotechnical and pharmaceutical fields.

DETAILED DESCRIPTION OF PREFERRED EXAMPLES

Figure 1:
FIG. 1 is an image of a fruiting body of *Antrodia camphorata* cultured by using a wood segment of *Cinnamomum camphora* (L.) Presl according to the present invention.

The present invention improves the fruiting chance on the wood segment in the manner of artificially inoculating *Antrodia camphorata* mycelia into a wood segment, so as to culture the thick and solid fruiting body having activities and ingredients comparable or superior to that of wild *Antrodia camphorata* in large scale. As natural *Antrodia camphorata* only grows on *Cinnamomum kanehirae* Hayata, if *Antrodia camphorata* strains are successfully inoculated into a wood segment from different tree species, a significant breakthrough would be made for the artificial wood segment culture technology.

According to the present invention, a culture method of *Antrodia camphorata* mycelia includes: fermenting a culture medium containing yeast at 5-35° C. for 3-30 days. Microorganisms in the culture medium are converted during fermentation, which is beneficial to the subsequent nutritional ingredients uptake of *Antrodia camphorata* culture; afterwards, adding wood flour to the fermented culture medium with stirring; next, placing the wood flour and the culture medium into a vessel; then, sterilizing the vessel containing the wood flour and the culture medium; and finally, inoculating *Antrodia camphorata* strains into the sterilized vessel containing the wood flour and the culture medium, and culturing at 5-35° C., to obtain a highly active mycelia.

According to the present invention, a culture method of a fruiting body of *Antrodia camphorata* includes: firstly, inoculating the matrix containing *Antrodia camphorata* mycelia into a wood segment; next, placing the wood segment inoculated with *Antrodia camphorata* mycelia in an environment where the temperature is 5-35° C., the humidity is 65-85% and the concentration of $CO_2$ is lower than 2%, and culturing for a period of time; afterwards, removing the matrix remained on the wood segment, then placing the wood segment in an environment where the temperature is 15-35° C., the humidity is 80-98% and the concentration of $CO_2$ is lower than 2%, and culturing for a period of time, to obtain a fruiting body of *Antrodia camphorata*. The matrix containing *Antrodia camphorata* mycelia can be a solid matrix or a liquid matrix.

According to the present invention, a culture method of a fruiting body of *Antrodia camphorata* includes: firstly, fermenting a culture medium containing yeast at 5-35° C. for 3-30 days; adding wood flour to the fermented culture medium with stirring; placing the wood flour and the culture medium into a vessel; sterilizing the vessel containing the wood flour and the culture medium; inoculating *Antrodia camphorata* strains into the sterilized vessel containing the wood flour and the culture medium, and culturing at 5-35° C., to obtain a highly active mycelia; inoculating the wood flour containing *Antrodia camphorata* mycelia into a wood segment; placing the wood segment inoculated with *Antrodia camphorata* mycelia in an environment where the temperature is 5-35° C., the humidity is 65-85% and the concentration of $CO_2$ is lower than 2%, and culturing for a period of time; and removing the matrix remained on the wood segment, and then, placing the wood segment in an environment where the temperature is 15-35° C., the humidity is 80-98% and the content of $CO_2$ is lower than 2%, and culturing for a period of time, to obtain a fruiting body of *Antrodia camphorata*.

The species of the wood segment suitable for the culture method for the fruiting body of *Antrodia camphorata* of the present invention include, but not limited to, *Cinnamomum kanehirai*, camphor tree, such as *Cinnamomum camphora* (L.) Presl and *Cinnamomum parthenoxylon* (Jack) Nees, Chinese camphor tree, or a miscellaneous tree, for example, *Acacia confusa* Merr., *Cinnamomum osmophloeum Kaneh, Cunninghamia lanceolata*, *Machilus kusanoi*, Maple, *Psidium guajava* L., *Betulaceae, Hamamelidaceae*, and *Fagaceae*, in which the species with hard woodiness is particularly preferred.

The method of the present invention is applicable to any species of *Antrodia camphorata* strains, for example, those have been deposited in the Institute of Food Science under the accession numbers: BCRC 35396, BCRC 35716, BCRC 35398 or BCRC 36401 which can be purchased freely.

The present invention is further described in detail with reference to the examples below, which are intended to exemplify the present invention, but not to limit the scope of the present invention.

EXAMPLES

Example 1

Culture of Fruiting Body of *Antrodia camphorata* by Using Wood Segment of *Cinnamomum camphora* (L.) Presl A culture medium containing yeast was fermented at 28° C. for 14 days. Microorganisms in the culture medium are converted during fermentation, which is beneficial to the subsequent nutritional ingredients uptake of *Antrodia camphorata*. Next, wood flour was added to the fermented culture medium with stirring. Then, the wood flour and the culture medium were placed in a flask, and the flask filled with the wood flour and the culture medium was sterilized at high temperature. And finally, the sterilized flask containing the wood flour and the culture medium was inoculated with *Antrodia camphorata* strains, and cultured at 28° C. for 2.5 months, to obtain mycelia.

A wood segment of *Cinnamomum camphora* (L.) Presl was inoculated with the cultured wood flour containing *Antrodia camphorata* mycelia, and then placed in an environment where the temperature is 5-35° C., the humidity is 65-85% and the concentration of $CO_2$ is lower than 2%, and cultured for 2.5 months. After the wood segment was infected with *Antrodia camphorata* mycelia, the wood flour remained on the wood segment was removed. And then, the wood segment was placed in an environment where the temperature is 15-35° C., the humidity is 80-98% and the concentration of $CO_2$ is lower than 2%, and cultured for 7 months, to obtain a fruiting body of *Antrodia camphorata*, as shown in FIG. 1. It can be clearly seen from FIG. 1 that, the fruiting body of *Antrodia camphorata* cultured according to the culture method of the present invention is thick and solid and has a configuration similar to that of a fruiting body of wild *Antrodia camphorata*. The analysis of the content of triterpenoids ingredient is described in detail hereinafter.

Example 2

Culture of Fruiting Body of *Antrodia camphorata* by Using Wood Segment of *Acacia confusa* Merr.

A culture medium containing yeast was fermented at 28° C. for 14 days. Microorganisms in the culture medium are converted during fermentation, which is beneficial to the subsequent nutritional ingredients uptake of *Antrodia camphorata*. Next, wood flour was added to the fermented culture medium with stirring. Afterwards, the wood flour and the culture medium were filled into a flask, and sterilized at high temperature. And finally, the sterilized flask containing the wood flour and the culture medium was inoculated with *Antrodia camphorata* strains, and cultured at 5-35° C. for 3 months, to obtain *Antrodia camphorata* mycelia.

Figure 2:
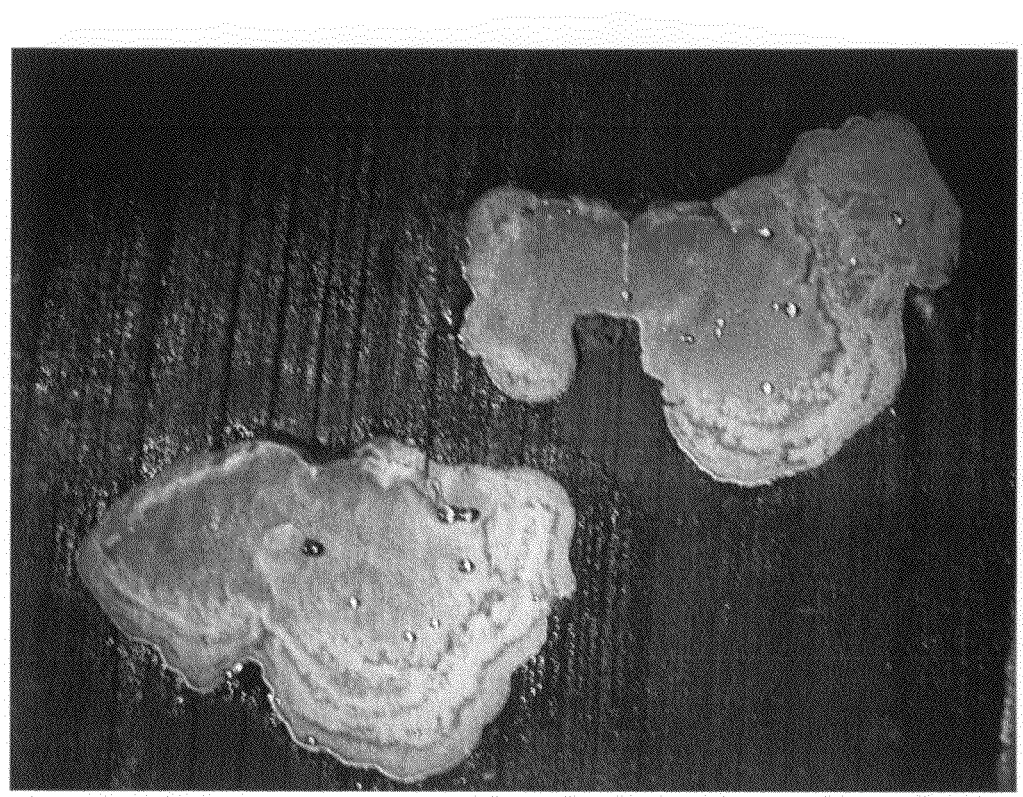
FIG. 2 is an image of a fruiting body of *Antrodia camphorata* cultured by using a wood segment of *Acacia confusa* Merr. according to the present invention.

A wood segment of *Acacia confusa* Merr. was inoculated with the cultured wood flour containing *Antrodia camphorata* mycelia, and then placed in an environment where the temperature is 5-35° C., the humidity is 65-85% and the concentration of $CO_2$ is lower than 2%, and cultured for 3 months. After the wood segment was infected with *Antrodia camphorata* mycelia, the wood flour remained on the wood segment was removed. Next, the wood segment was placed in an environment where the temperature is 15-35° C., the humidity is 80-98% and the content of $CO_2$ is lower than 2%, and cultured for 6 months, to obtain a fruiting body of *Antrodia camphorata*, as shown in FIG. 2. It can be clearly seen from FIG. 2 that, the fruiting body of *Antrodia camphorata* cultured according to the culture method of the present invention is thick and solid and has a configuration similar to that of a fruiting body of wild *Antrodia camphorata*. The analysis of the content of triterpenoids ingredient is described in detail hereinafter.

Example 3

Culture of a Fruiting Body of *Antrodia camphorata* by Using Wood Segment of *Cinnamomum kanehirae* Hayata A culture medium containing yeast was fermented at 5-35° C. for 3-30 days. Microorganisms in the culture medium are converted during fermentation, which is beneficial to the subsequent nutritional ingredients uptake of *Antrodia camphorata*. Next, wood flour was added to the fermented culture medium with stirring. Afterwards, the wood flour and the culture medium were filled into a flask, and sterilized at high temperature. And finally, the sterilized flask containing the wood flour and the culture medium was inoculated with *Antrodia camphorata* strains, and cultured at 5-35° C. for 2.5 months, to obtain mycelia.

Figure 3:
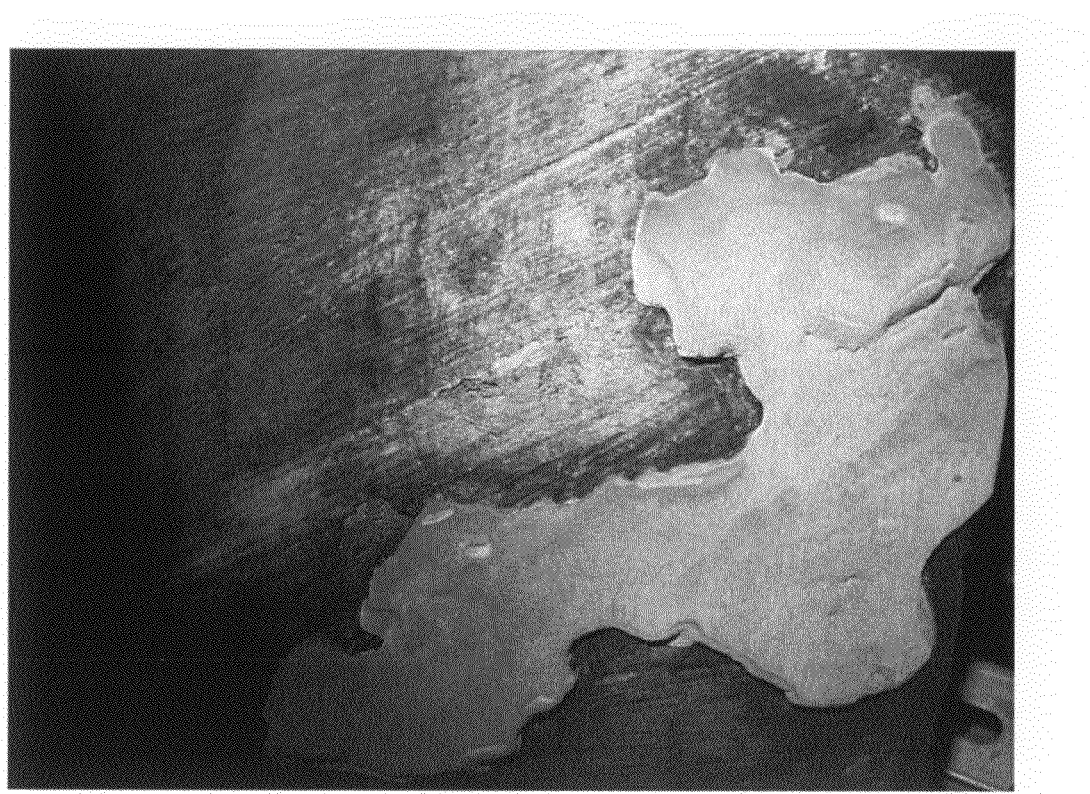
FIG. 3 is an image of a fruiting body of *Antrodia camphorata* cultured by using a wood segment of *Cinnamomum kanehirae* Hayata according to the present invention.

A wood segment of *Cinnamomum kanehirae* Hayata was inoculated with the cultured wood flour containing *Antrodia camphorata* mycelia, and then placed in an environment where the temperature is 5-35° C., the humidity is 65-85% and the concentration of $CO_2$ is lower than 2%, and cultured for 2.5 months. After the wood segment was infected with *Antrodia camphorata* mycelia, the wood flour remained on the wood segment was removed. Next, the wood segment was placed in an environment where the temperature is 15-35° C., the humidity is 80-98% and the concentration of $CO_2$ is lower than 2%, and cultured for 8 months, to obtain a fruiting body of *Antrodia camphorata*, as shown in FIG. 3. It can be clearly seen from FIG. 3 that, the fruiting body of *Antrodia camphorata* cultured according to the culture method of the present invention is thick and solid and has a configuration similar to that of a fruiting body of wild *Antrodia camphorata*. The analysis of the concentration of triterpenoids ingredient is described in detail hereinafter.

Example 4

Comparison of Ingredient Contents of *Antrodia camphorata* Cultured According to the Present Invention, Wild *Antrodia camphorata*, and Commercial Available *Antrodia camphorata*

The fingerprint spectrum of each sample by high pressure liquid chromatography (HPLC) is analyzed based on the principle that the same species has same ingredients. The fingerprint spectra are used to compare the homology between the samples, and analyze and compare the total contents of the ingredients, so as to evaluate the quality of each sample.

Preparation of the Sample Solution

Five samples, including the fruiting body of wild *Antrodia camphorata*, the powder content in commercial available capsule of *Antrodia camphorata*, and the artificial fruiting body of *Antrodia camphorata* cultured according to the culture method of the present invention on three different wood segments, i.e., *Cinnamomum kanehirae* Hayata, *Cinnamomum camphora* (L.) Presl, and *Acacia confusa* Merr. (Examples 1 to 3) were analyzed in the experiment. Firstly, these five samples were fine cut or ground into powder, placed in a constant temperature oven of 60° C. and dried for 20 hours continuously, then taken out and cooled in a dryer. Next, 800 mg of each sample was weighed accurately and placed into a 25 mL volumetric flask, and then added 15 ml of methanol accurately and capped tightly. Afterwards, the volumetric flask was shaken and suctioned in an ultrasonic shaker for 3 hours, and the suctioned solution was filtered through a 0.45 μm filter membrane, to get a clear liquid for being used as a sample solution for analysis.

High Pressure Liquid Chromatography:

The high pressure liquid chromatograph used in the analysis is HITACHI D-7000 series, including: a pump: L-7100, a detector: L-7420, an autosampler: L-7200, in which the HPLC column RP-18 has a length of 250 mm and an inner diameter of 4.6 mm (particle size of 5 μm).

Analysis conditions include: flow rate: 1 mL/min, detection absorption wavelength: UV 210 nm, injection volume: 25 μL, analysis time: 190 min. For gradient elution, two solvent systems are used as mobile phases: mobile phase A: 10% of acetonitrile (containing 1% of phosphoric acid), mobile phase B: 100% of acetonitrile (containing 1% of phosphoric acid). Gradient elution conditions are shown in Table 1.

TABLE 1

Gradient elution conditions of HPLC mobile phase

| Time (min) | Mobile phase A | Mobile phase B | Flow (mL/min) |
|---|---|---|---|
| 0.0 | 100.0 | 0.0 | 1.0000 |
| 5.0 | 100.0 | 0.0 | 1.0000 |
| 10.0 | 70.0 | 30.0 | 1.0000 |
| 15.0 | 55.0 | 45.0 | 1.0000 |
| 25.0 | 55.0 | 45.0 | 1.0000 |
| 30.0 | 50.0 | 50.0 | 1.0000 |
| 45.0 | 50.0 | 50.0 | 1.0000 |
| 55.0 | 40.0 | 60.0 | 1.0000 |
| 70.0 | 40.0 | 60.0 | 1.0000 |
| 80.0 | 20.0 | 80.0 | 1.0000 |
| 90.0 | 0.0 | 100.0 | 1.0000 |
| 145.0 | 0.0 | 100.0 | 1.0000 |
| 165.0 | 100.0 | 0.0 | 1.0000 |
| 190.0 | 100.0 | 0.0 | 1.0000 |

Absorption peak area is automatically calculated by build-in software, where the peak rejection level is set at 200,000, and the one with an absorption peak area lower than 200,000 is considered to be noises, and is abandoned not to be calculated; the one with an absorption peak area reached 200,000, but with an irregular absorption peak is also abandoned by manual screen; and finally, the reliable absorption peak area of each sample solution for analysis is added, and compared with one another, to carry out quality evaluation.

As shown in Table 2 below, the integration of the total absorption peak area for the fruiting body of wild *Antrodia camphorata* is 139,983,370; the integration of the total area for the fruiting body of *Antrodia camphorata* cultured on the wood segment of *Acacia confusa* Merr. is 76,165,715; the integration of the total area for the fruiting body of *Antrodia camphorata* cultured on the wood segment of *Cinnamomum camphora* (L.) Presl is 111,356,206; the integration of the total area for the fruiting body of *Antrodia camphorata* cultured on the wood segment of *Cinnamomum kanehirae* Hayata is 152,760,267; and the integration of the total area for commercial available capsule of *Antrodia camphorata* is 21,126,138, which is far below those of the four samples.

TABLE 2

Absorption peak areas for assay solutions of different types of artificial cultured fruiting bodies of *Antrodia camphorate*

| Wavelength: 210 nm<br>Sample Name | Absorption intensity:<br>1300 mV<br>Total Absorption<br>Peak Area* |
|---|---|
| Commercial available *Antrodia camphorata* | 21,126,138 |
| Wild *Antrodia camphorata* | 139,983,370 |
| Artificial cultured *Antrodia camphorata* by using a miscellaneous tree (*Cinnamomum camphora* (Linn.) Presl) | 111,356,206 |
| Artificial cultured *Antrodia camphorata* by using a miscellaneous tree (*Acacia confusa* Merr) | 76,165,715 |
| Artificial cultured *Antrodia camphorata* by using a miscellaneous tree (*Cinnamomum kamhirai* Hay) | 152,760,267 |

*Rejection level of the absorption peak area: 200,000;
*Recording time limit: 180 min.

Results

Figure 4:
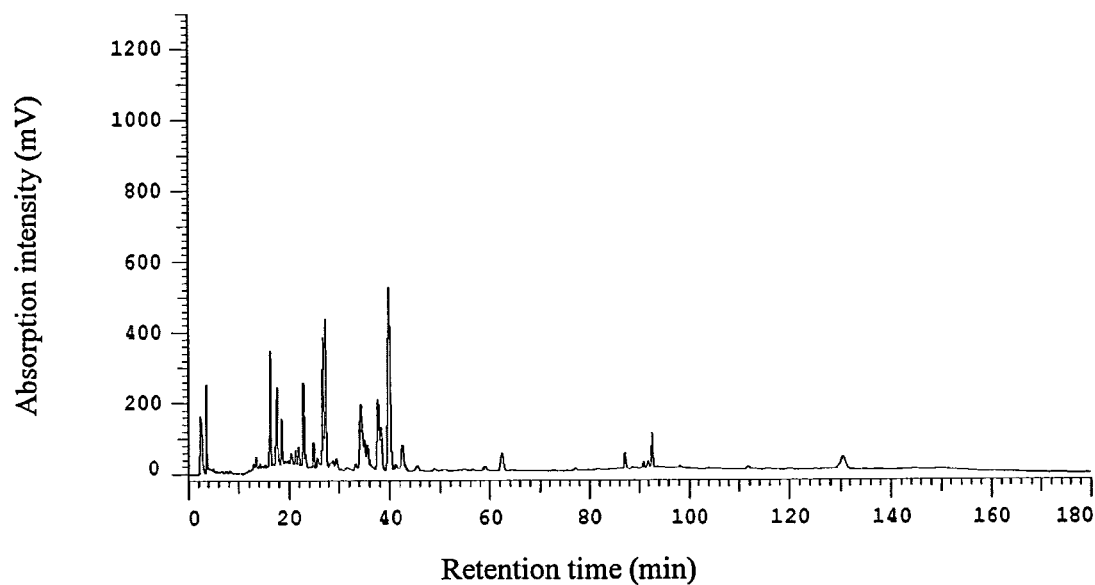
FIG. 4 is an HPLC spectrum of the fruiting body of *Antrodia camphorata* cultured by using a wood segment of *Cinnamomum camphora* (L.) Presl according to the present invention.
Figure 5:
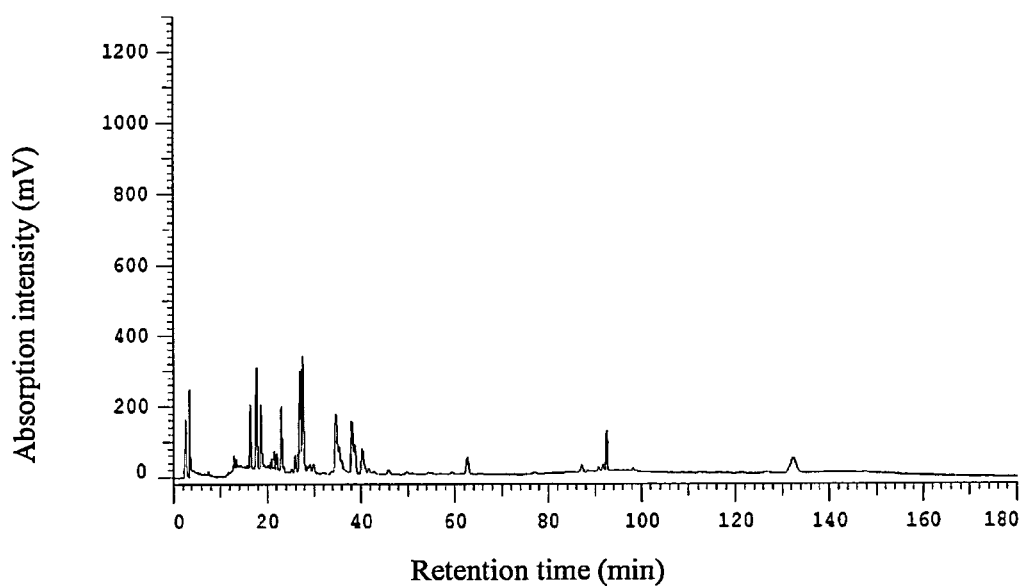
FIG. 5 is an HPLC spectrum of the fruiting body of *Antrodia camphorata* cultured by using a wood segment of *Acacia confusa* Merr. according to the present invention.
Figure 6:
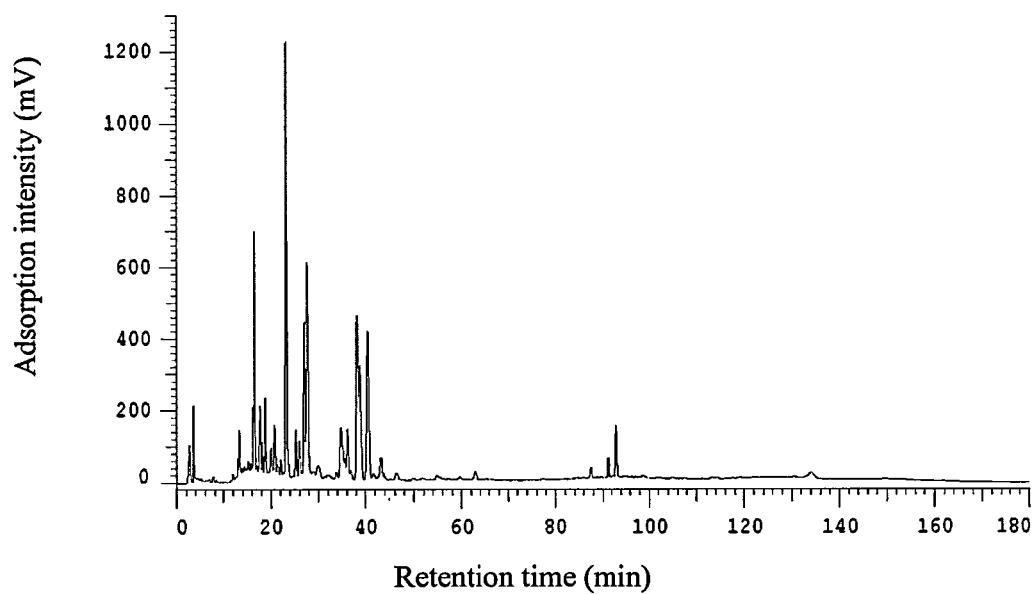
FIG. 6 is an HPLC spectrum of the fruiting body of *Antrodia camphorata* cultured by using a wood segment of *Cinnamomum kanehirae* Hayata according to the present invention.

The spectra of these five samples are analyzed at the same absorption intensity (1300 mV) and the same retention time (180 min). The respective HPLC spectra of *Cinnamomum camphora* (L.) Presl, *Acacia confusa* Merr., and *Cinnamomum kanehirae* Hayata are shown in FIGS. 4, 5 and 6.

Figure 7:
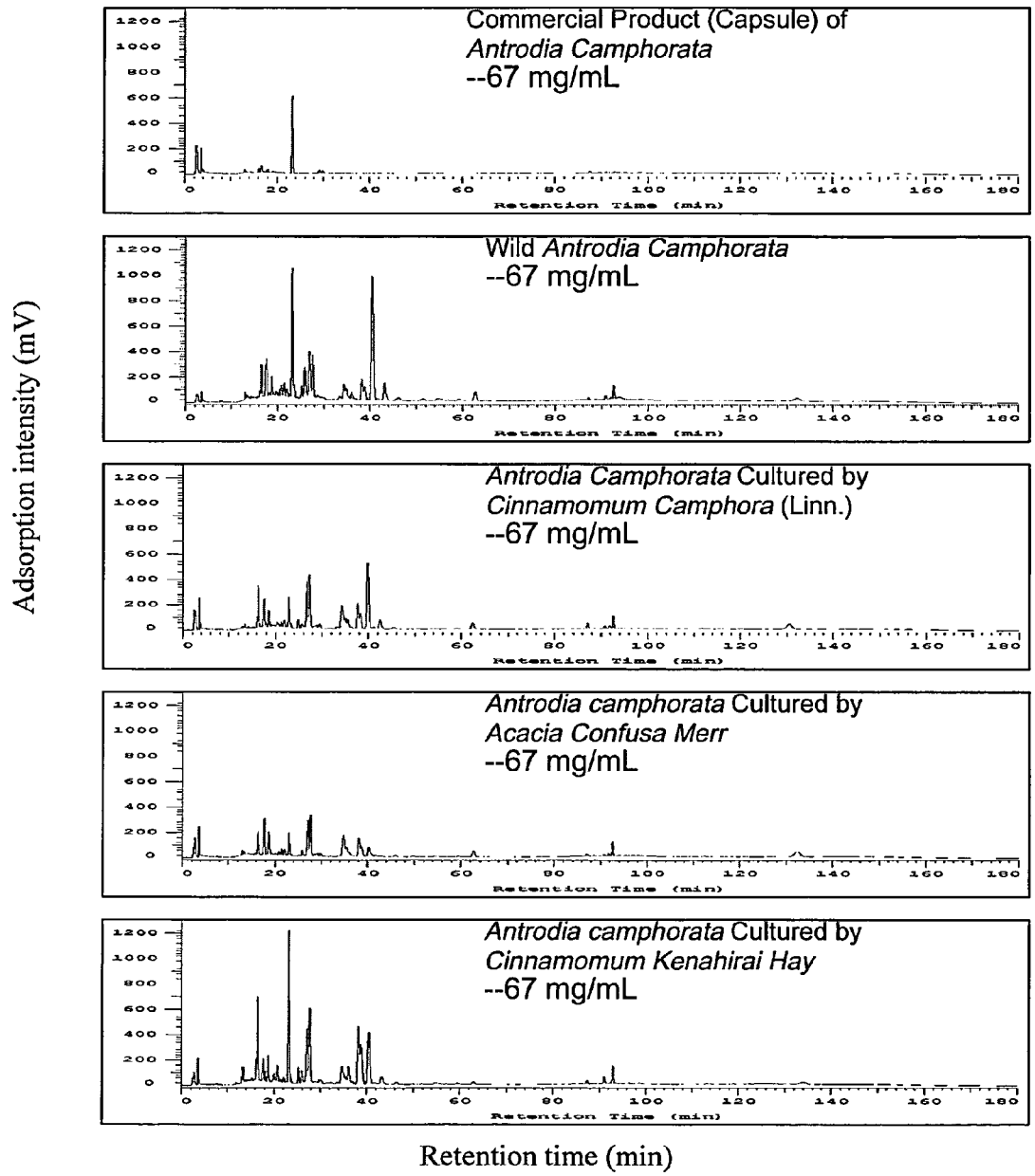
FIG. 7 is an overlapping comparison of HPLC spectra of a commercial product (capsule) of *Antrodia camphorata*, a fruiting body of wild *Antrodia camphorata*, and fruiting bodies of *Antrodia camphorata* cultured by *Cinnamomum camphora* (L.) Presl, *Acacia confusa* Merr., and *Cinnamomum kanehirae* Hayata according to the present invention.

Additionally, by using these five samples, fingerprint spectra of the commercial product (capsule) of *Antrodia camphorata*, the fruiting body of wild Antrodia camphorata, and the artificial fruiting bodies of *Antrodia camphorata* cultured by three different wood segments, i.e., *Cinnamomum camphora* (L.) Presl, *Acacia confusa* Merr., and *Cinnamomum kanehirae* Hayata are compared by overlapping, as shown in FIG. 7. It can be observed from the overlapped figure that, the fingerprint spectra of the three artificial cultured fruiting bodies of *Antrodia camphorata* have the same absorption group at the same position (i.e. at the same retention time) with the fruiting body of wide *Antrodia camphorata*, except that there are some differences in absorption intensities; and the fingerprint spectrum of commercial available product of *Antrodia camphorata* is significantly different from those of the three samples, and the absorption intensity is very weak. The result obtained by comparing and analyzing the overlapped figure clearly shows that, the artificial fruiting bodies of *Antrodia camphorata* cultured by *Cinnamomum kanehirae* Hayata, *Cinnamomum camphora* (L.) Presl, *Acacia confusa* Merr. are homologous to the fruiting body of wild *Antrodia camphorata*, which indicates that the fruiting bodies of *Antrodia camphorata* of the present invention cultured by different wood segments have similar triterpenoids ingredients and the same physiological activities and usages with the fruiting body of wild *Antrodia camphorata*.

It can be observed from the analysis results that, the present invention provides an artificial culture method of the fruiting body of *Antrodia camphorata* in large scale and the cultured fruiting body of *Antrodia camphorata* is thick and solid, and has the active ingredients identical with or superior to those of wild or commercial available artificial-cultured *Antrodia camphorata*. Therefore, the present invention is a significant breakthrough in the technology of artificial culture of the fruiting body of *Antrodia camphorate*.

Other Implementation Aspects

Although the present invention is disclosed as above with preferable examples, it is not limited to the disclosure of the examples, and it will be apparent to those skilled in the art that various alternations and modifications can be made without departing from the scope or spirit of the invention. Therefore, the protection scope of the present invention depends on those defined by the scope of the following claims.

I claim:

1. A method for producing a fruiting body of *Antrodia camphorata*, comprising:
   (a) fermenting a culture medium containing yeast at 15-35° C. for 3-30 days;
   (b) adding wood flour to the fermented culture medium with stirring;
   (c) placing the wood flour and the culture medium into a vessel;
   (d) sterilizing the vessel containing the wood flour and the culture medium;
   (e) inoculating *Antrodia camphorata* strains into the sterilized vessel containing the wood flour and the culture medium, and culturing at 15-35° C., to obtain *Antrodia camphorata* mycelia;
   (f) inoculating the wood flour containing the *Antrodia camphorata* mycelia into a wood segment;
   (g) placing the wood segment inoculated with *Antrodia camphorata* mycelia in an environment where the temperature is 15-35° C. and the humidity is 65-85%, and culturing for a period of time; and
   (h) removing the wood flour remaining on the wood segment, then placing the wood segment in an environment where the temperature is 15-35° C. and the humidity is 80-98%, and culturing for a period of time, to obtain a fruiting body of *Antrodia camphorata;* wherein said wood segment is obtained from *Cinnamomum camphora* (L.) Presl *Acacia confusa* Merr., or *Cunninghamia lanceolata.*

2. The method of claim 1, wherein the wood segment in Step (g) is cultured in an environment wherein the temperature is 25-30° C. and the humidity is 75-85%.

3. The method of claim 1, wherein the wood segment in Step (h) is cultured in an environment wherein the temperature is 26-30° C. and the humidity is 90-98%.

4. The method of claim 1, wherein the culture time in Step (g) is at least one month.

5. The method of claim 1, wherein the culture time in Step (h) is at least three months.

* * * * *